US007557685B2

(12) United States Patent
Nellessen

(10) Patent No.: US 7,557,685 B2
(45) Date of Patent: Jul. 7, 2009

(54) MINERAL SUPPLEMENT COW MAGNET

(76) Inventor: John Nellessen, 7 Cornwallis, Irvine, CA (US) 92620

( * ) Notice: Subject to any disclaimer, the term of this patent is extended or adjusted under 35 U.S.C. 154(b) by 21 days.

(21) Appl. No.: 11/527,801

(22) Filed: Sep. 22, 2006

(65) Prior Publication Data

US 2008/0074222 A1 Mar. 27, 2008

(51) Int. Cl.
*H01F 7/02* (2006.01)
*A61N 2/00* (2006.01)

(52) U.S. Cl. ........................................ 335/302; 600/12

(58) Field of Classification Search ..................... 600/9, 600/12; 335/302-306

See application file for complete search history.

(56) References Cited

U.S. PATENT DOCUMENTS 2,613,246 A 10/1952 Spodig
2,853,075 A 9/1958 Hoffman et al.
3,005,458 A 10/1961 Brook et al.
3,014,751 A 12/1961 Smith
3,187,239 A 6/1965 Rosenberger et al.
3,206,657 A 9/1965 Moriya
4,283,698 A 8/1981 Fujisawa
4,303,062 A 12/1981 Vars
4,544,904 A 10/1985 Tarachand
4,749,978 A 6/1988 Imamura et al.
4,888,068 A 12/1989 Tokunaga et al.
4,992,768 A 2/1991 Mozis et al.
5,096,763 A 3/1992 Ogata et al.
5,128,644 A 7/1992 Nellessen
5,663,701 A 9/1997 Kaura

FOREIGN PATENT DOCUMENTS

CN 1400722 A * 3/2003

OTHER PUBLICATIONS

Arnox Permanent Magnets, Hard Ferrite Material, Arnold Magnetics, Ltd, Apr. 2003; www.arnoldmagnetics.com.*
RoHS (Restriction of Hazardous Substances) Comliance with European Directive 2000/95/EC, Arnold Magnetic Technologies, Jul. 28, 2006; www.arnoldmagnetics.com.*

* cited by examiner

*Primary Examiner*—Ramon M Barrera

(57) ABSTRACT

A cow magnet is provided having minerals that have been found useful for good health. A cow magnet of Ferrous Oxide (FeO) and stable Strontium (Sr) is discovered to be healthy. Stable Strontium (Sr) is discovered to be used by the bovine body to increase bone growth and strength. Iron (Fe) is known to be used by the bovine body for healthy red blood cells. The magnet is sintered to control the trace amounts of these elements released into the stomach. The polarity pattern is discovered for SrFe type magnets so that a nail will be held parallel to the length of the magnet and at the maximum strength. This pole pattern has been discovered to turn a nail parallel to the length of the magnet if the nail is placed on the magnet perpendicular to the length. This pole pattern also prevents a nail from being held along the length with the sharp tip sticking out past the end of the magnet. This prevents damage to the ruminator's first stomach. The strength is the same as the standard AlNiCo 5 magnets. The cost is less than AlNiCo magnets. The Aluminum in AlNiCo is discovered to be toxic. Therefore the Strontium Ferrous Oxide magnets (SrFeO) are more healthy.

5 Claims, 3 Drawing Sheets

MINERAL SUPPLEMENT COW MAGNET

BACKGROUND

1. Technical Field of the Invention

This invention generally relates to bovine health, primarily to the prevention of "Hardware Disease" in cattle, and secondarily to prevention of toxic Al blood and bone poisoning, thirdly to strengthening of bones, fourthly to healthy red blood cells.

2. Description of Prior Art

Cows have been known to accidentally eat fencing staples, bailing wire remnants, nails, etc. while grazing. Cow magnets are administered orally to cows to attract and retain ferrous material within the Rumen (upper stomach). The magnet is heavy enough to prevent passage from the Rumen. The magnet remains in the Rumen collecting iron pieces and particles and retaining them within the Rumen for the entire life of the cow. Retention of sharp iron pieces within the Rumen greatly reduces the possibility of damage to other more delicate, vital organs. Damage to intestines, organs, etc. caused by ingestion of iron objects often causes the animal to stop eating and eventually expire. The cause of death is then categorized by veterinarians as "Hardware Disease." Various types of cow magnets have been available over the past forty years and have contributed greatly to the prevention of Hardware Disease.

Heretofore cow magnets have appeared to be made of non-toxic metals. They have however not adequately fulfilled the necessity for the magnet to be non-toxic to the cow. They also have not been made of minerals to supplement the cow's health. Prior art suffers as follows:

(1) The current standard cow magnet is made of Aluminum Ni and Cobalt (AlNiCo). The alloy is largely Aluminum, $Al_{72}Ni_{21}Co_9$. Increasing numbers of studies are finding Al to be a toxic element. There are over 2000 references in the National Library of Medicine on adverse effects of Aluminum. (www.hbci.com/~wenonah/hydro/al.htm). The U.S. Agency for Toxic Substances and Disease Registry (ATSDR),(http://www.atsdr.cdc.gov/) is a federal public health agency of the U.S. Department of Health and Human Services.

According to the ATSDR Aluminum has been shown to be harmful to unborn and developing animals because it causes delays in skeletal and neurological development.

Aluminum has also been shown to cause lower birth-weights in animals.

Aluminum is found to neutralize stomach acids resulting in slowed digestion and constipation.

Studies show that humans with Alzheimer's disease have more Aluminum than usual in their brains.

Infants and adults who received large doses of Al as a treatment for another problem have developed bone diseases, which suggests that Al may cause skeletal problems.

The following charts (deleted available upon request) first show Aluminum toxic levels. Later under advantages we compare Aluminum with Strontium toxic levels, according to the ATSDR. Allowable levels of these two minerals before becoming seriously toxic are:

1) Al serious toxic levels average 350 mg/kg of body weight/day

2) Sr serious toxic levels average 2300 mg/kg of body weight/day

The ATSDR studies to date conclude that Al is 6 times more toxic than Sr. ATSDR Studies to date conclude that Aluminum is 6 times more toxic than Strontium. http://www.atsdr.cdc.gov/toxprofiles/tp22.html (2) The fear that ferrite magnets are toxic has long been assumed because:

a) Toxic Barium was used for a long time to make ferrite magnets.

b) Strontium was thought to be radioactive by many consumers.

Ferrite type magnets before 1987 were made using Barium. Ferrite magnets earned the reputation among dairy veterinarians for being toxic to cows. Gradually some factories have replaced Barium with Strontium in ferrite magnets. However, there is still a fear associated with radio-active type Strontium 89 and 90. This fear has kept veterinarians from using cow magnets made with stable Strontium 84, 86, 87 and 88.

(3) Al is not a mineral that animals can use for healthy growth.

(4) Nickel (Ni) found in the AlNiCo type magnets is a slightly toxic element. Nickel is a strongly linked with causing several diseases. It is toxic to the cardiovascular system, as well as being carcinogenic to the stomach. http://database-.healthandenvironment.org/index.cfm?toxinID=2399

(5) Cow magnets made with Barium Ferrite are highly toxic. Barium causes difficulties in breathing, Increased blood pressure, Changes in heart rhythm, Stomach irritation, Brain swelling, Muscle weakness, Damage to the liver, kidney, heart, and spleen http://www.skyhighway.com/~chemtrails/docs/bariumhealth.htm (6) Some prior art Barium Ferrite cow magnets were only be magnetized in a direction that caused some sharp long objects to be held dangerously perpendicular to the magnet surface.

(7) Ferrite magnets are normally machined in blocks, rings and disks with sharp edges which could damage the bovine rumen.

(8) Prior to 2006 Strontium Ferrite magnets were not available in long rods to be magnetized to hold metal parts safely in a cow magnet application.

(9) The magnetic assembly by Fujisawa U.S. Pat. No. 4,283,698 and other "assembly" type magnets suffer from the same weakness. They may be magnetically proper, but structurally weak and could be a great danger to the cows. The structural weakness may not become apparent until stomach acids dissolve some of the connecting parts.

(10) Magnetic assemblies suffer from using more than one part.

(11) Some older designs are made of a magnetically inferior material such as AlNiCo of various grades, which is more subject to demagnetization.

(12) Multiple pole patterns with more than 4 poles cause a nail to lay parallel to the cow magnet, but the sharp tip of the nail extends beyond the end of the magnet. The nail is held firmly in place magnetically and may cause damage to the cows first stomach.

SUMMARY OF THE INVENTION

According to the present invention, a mineral supplement cow magnet comprises a solid piece of SrFeO with a dosage of only non-toxic and healthy minerals. The magnet in accordance with the present invention is made of or coated with healthy minerals for cows. The magnet in accordance with the present invention may have pole patterns configured to localize metal fragments at particular locations on its surface, so as to minimize the risk of injuring the cow's stomach. The nails will be pulled to a position parallel to the length of the magnet and centered along the length. The invention is dimensioned and weighted so as to not pass on to a cow's intestines. The magnet material having stronger magnetic properties than current cow magnets.

Objects and Advantages

1) According to the ASTDM study below, Strontium is 6 times less toxic than Aluminum. Strontium is a naturally occurring element. Naturally occurring strontium is not radioactive and is either referred to as stable Strontium or Strontium. Strontium in the environment exists in four stable isotopes, $^{84}$Sr (read as strontium eighty-four), $^{86}$Sr, $^{87}$Sr, $^{88}$Sr. Any of which are non-toxic in small amounts. According to the ASTDM, "Exposure to low levels of stable strontium has not been shown to affect adult health." http://www.atsdr.cdc.gov/toxprofiles/tp159.pdf According the National Research Council (NRC) Aluminum is toxic at levels of 1000 mg/kg of body weight. Strontium is not toxic until 2000 mg/kg. Aluminum is twice as toxic as Strontium, in this study:

National Research Council (NRC) 1996. Nutrient requirements for beef cattle (7$^{th}$ Ed.). National Academy Press, Washington, D.C.

Vitamin and Mineral Requirements and Maximum Tolerable Concentrations$^{ab}$

| | Unit | Gestation | Lactation | Max. Tolerable Concentration |
|---|---|---|---|---|
| Vitamins required by beef cattle | | | | |
| A | IU/kg | 2800 | 3900 | — |
| D | IU/kg | 275 | 275 | — |
| Minerals required by beef cattle | | | | |
| Calcium | % | See tables 1-4 | See tables 1-4 | 2 |
| Chlorine | % | — | — | — |
| Chromiumc | mg/kg | — | — | 1,000.00 |
| Cobalt | mg/kg | 0.1 | 0.1 | 10 |
| Copper | mg/kg | 10 | 10 | 100.00 |
| Iodine | mg/kg | 0.5 | 0.5 | 50 |
| Iron | mg/kg | 50 | 50 | 1,000.00 |
| Magnesium | % | 0.12 | 0.2 | 0.4 |
| Manganese | mg/kg | 40 | 40 | 1,000.00 |
| Molybdenumc | mg/kg | — | — | 5 |
| Nickelc | mg/kg | — | — | 50.00 |
| Phosphorus | % | See tables 1-4 | See tables 1-4 | 1 |
| Potassium | % | 0.6 | 0.7 | 3 |
| Selenium | mg/kg | 0.1 | 0.1 | 2 |
| Sodium | % | 0.07d | 0.1 | — |
| Sulfur | % | 0.15 | 0.15 | 0.4 |
| Zinc | mg/kg | 30 | 30 | 500 |
| Minerals toxic to beef cattle | | | | |
| Aluminum | mg/kg | — | — | 1,000.00 |
| Arsenic | mg/kg | — | — | 50.0e |
| Bromine | mg/kg | — | — | 200.00 |
| Cadmium | mg/kg | — | — | 0.5 |
| Fluorine | mg/kg | — | — | 40.0f |
| Lead | mg/kg | — | — | 30 |
| Mercury | mg/kg | — | — | 2 |
| Strontium | mg/kg | — | — | 2,000.00 |

New data supports SrFe cow magnets. My previous patent U.S. Pat. No. 5,128,644, July 1992, Nellessen, a SrFe magnet assembly type cow magnet, has been tested for over 10 years in cows. No muscular growth losses, no bone loss, no nervous system disorders, no metabolism disorders, or any of the disorders associated with Aluminum, were found. The past fears of Barium being used in ferrite magnets can be dispelled.

2) The past fears of stable Strontium 88 causing the same health problems as radioactive Strontium 90 are being now dispelled.

3) Sr has been discovered used by the animal body for stopping bone absorption, increasing bone growth, stopping and reversing Osteoporosis, decreasing cavities in teeth, decreasing arthritis, according to World Health Net (http://www.worldhealth.net/p/273,5736.html). Stable Strontium is also used to reduce radio-active Strontium 90 levels in the body. According to http://www.y2khealthanddetox.com/Osteoporosis.htm, "Early clinical trials' results led researchers to speculate that Strontium increased osteoblast activity." Fe has been long know for its use in the body for healthy red blood cells. Therefore SrFe cow magnets supply minerals used by the body in levels that are non-toxic.

4) No Nickel is used in my invention. Therefore stomach cancer is not a concern.

5) No Barium is used in my invention. Therefore we avoid difficulties in breathing, Increased blood pressure, Changes in heart rhythm, Stomach irritation, Brain swelling, Muscle weakness, Damage to the liver, kidney, heart, and spleen.

6) The magnetization direction has been solved by making the North pole, South pole pattern so that a nail will be help parallel to the length of the invention, not perpendicular.

7) No sharp edges are used in my invention. My invention is pill shaped. Now a method for making pill shaped rods of SrFe type magnets has been found.

8) My invention is one piece. Therefore, there is no assembly to fall apart in my invention.

9) My invention is one piece. Therefore the omission of elements reduces assembly time labor, parts costs and risk of failure due to a defective part.

10) My invention is made of SrFeO with an Hci of 2500-3000 Oersteds. Therefore it will not demagnetize as easy as the AlNiCo type with 650 Oersteds.

11) My invention discovered the pole pattern of 4 poles through the diameter works best. When a nail is introduced this pole pattern will turn it and hold it parallel to the length of the magnet. Additionally it will pull the nail to be centered on the length of the magnet. Therefore, the nail does not extend past the end of the magnet and is thereby protected by the round end of the magnet from damaging the cow's first stomach.

While many devices have attempted to adequately account for these factors, none have successfully done so. The need exists, therefore, for a durable yet non-toxic cow magnet possessing a relatively strong magnetic field that may be easily introduced into the stomach but that cannot pass into a cow's intestines, which safely collects metal fragments while being inexpensive to construct.

DRAWING FIGURES

In the drawings a dotted line represents the dividing line between North Pole and South Pole.

REFERENCE NUMERALS IN DRAWINGS

1 Cow Magnet
2 Zn (mineral) coating

DESCRIPTION—FIGS. 1, 2, 3—PREFERRED EMBODIMENT

Figure 1:
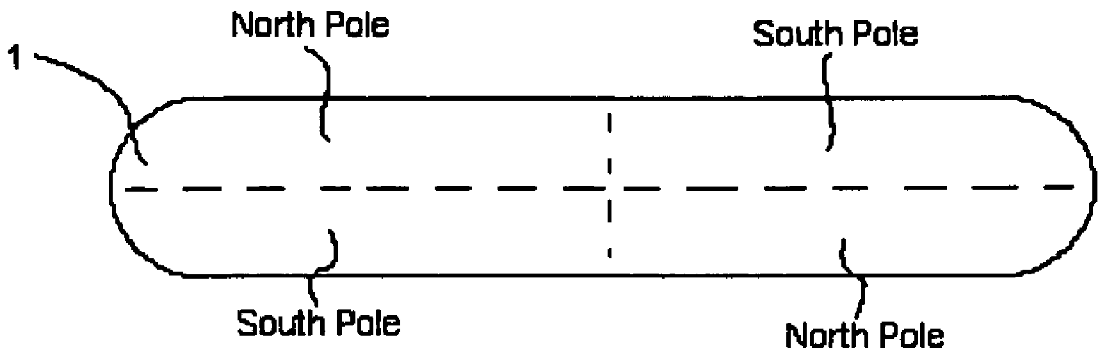
FIG. 1 shows a side view of the preferred embodiment.
Figure 2:
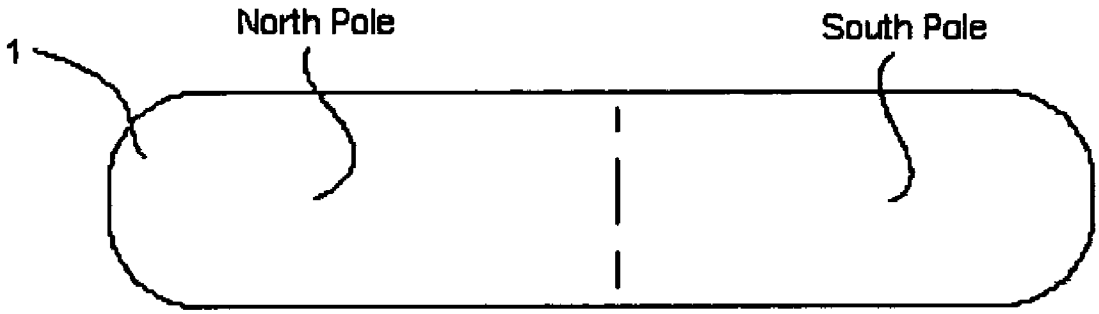
FIG. 2 shows a top view of the preferred embodiment.
Figure 3:
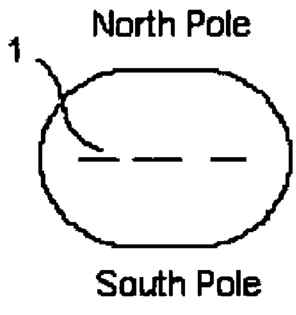
FIG. 3 shows an end view of the preferred embodiment.

A preferred embodiment of the cow magnet of the present invention is illustrated in FIGS. 1, 2, 3. The magnet is made of the minerals useful to the body, such as, Sr and Fe with a few trace elements. The Sr must be stable Sr such as Sr84, Sr86, Sr87, Sr88 (not radioactive Sr89 or Sr90). The metals are sintered to form tight alloy matrix structure. The pressing is done in a coil to create a preferred direction of magnetization. The pole pattern is 6 poles to create no place on the magnet where a nail could balance perpendicular to the length of the magnet. This pole pattern has been discovered to always pull the magnet parallel to the magnet length. The pole pattern also has a stronger pulling force. The magnet is pill shaped for easy insertion down the cow's throat. The preferred surface is smooth.

FIGS. 4-9—Additional Embodiments

Figure 4:
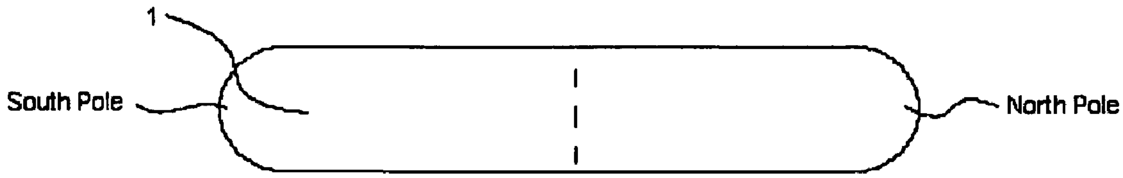
FIG. 4 shows a side view of an alternate magnetic orientation, magnetization and alternate pill shape of the preferred embodiment.
Figure 5:
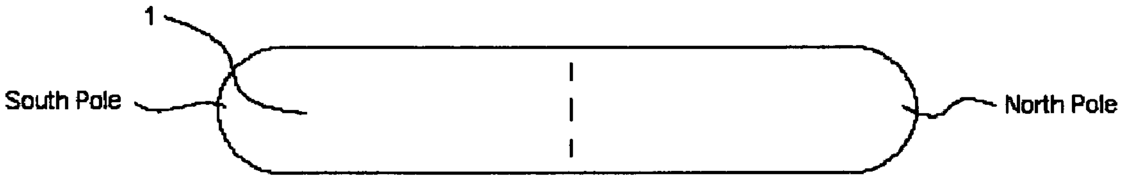
FIG. 5 shows a reverse side view of an alternate magnetic orientation, magnetization and alternate pill shape of the preferred embodiment.
Figure 6:
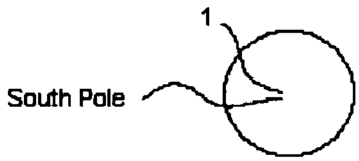
FIG. 6 shows an end view of an alternate magnetic orientation, magnetization and alternate pill shape of the preferred embodiment.
Figure 7:
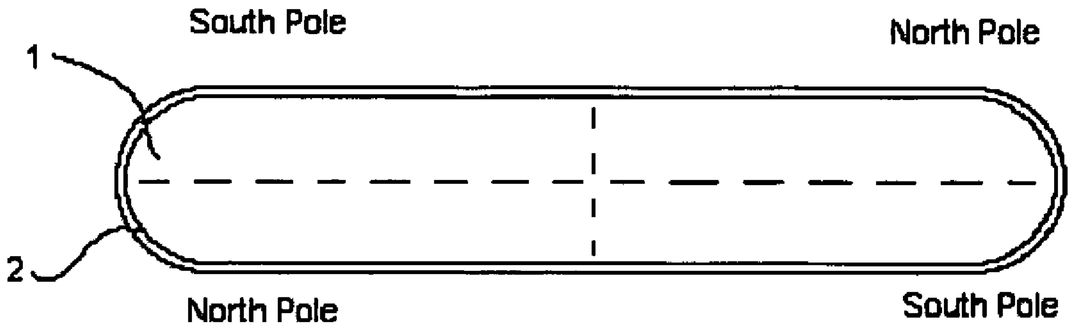
FIG. 7 shows a side view of the preferred embodiment with a Zn coating.
Figure 8:
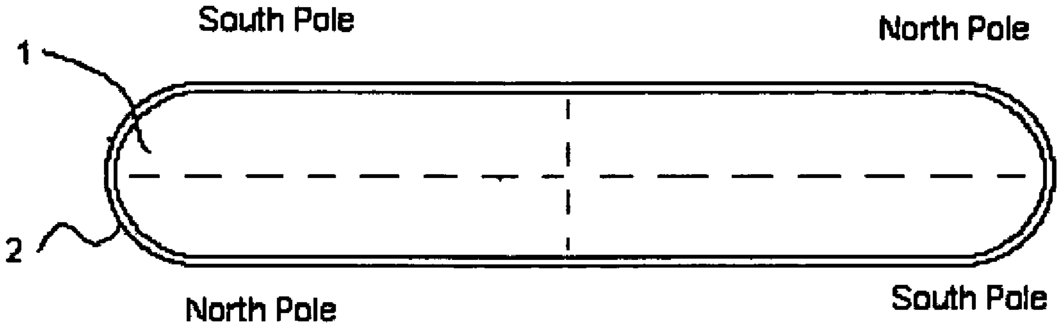
FIG. 8 shows a top view of the preferred embodiment with a Zn coating.
Figure 9:
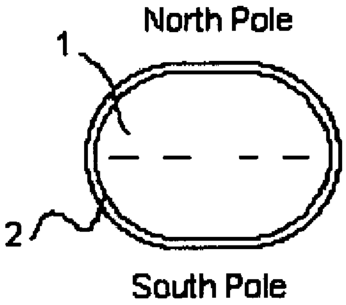
FIG. 9 shows an end view of the preferred embodiment with a Zn coating.

Additional Embodiments are shown in FIGS. 4, 5 & 6. The material is the same as the preferred embodiment. The magnetization pattern is with 2 poles. One pole on each end of the magnet. This magnetization has a weaker pulling force than the preferred embodiment.

Alternative Embodiments

There are various possible pill shapes. There are various surface treatments of healthy minerals. While the invention has been described in five embodiments, it is to be understood that the words which have been used are words of description rather than limitation, and that changes may be made within the purview of the appended claims without departing from the true scope and spirit of the invention in its broader aspects.

Advantages

The nutritional value of Sr is discovered to help bone growth and strength. The polarity pattern is discovered for a SrFe type magnet so that a nail will be held along parallel to the length of the magnet and pulled towards the center of the length. This pole pattern has been discovered to turn a nail parallel to the length of the magnet if the nail is placed on the magnet perpendicular to the length. Furthermore, this pole pattern also prevents a nail from being held along the length of the magnet with the sharp nail tip sticking out the end of the magnet. The magnetic properties of this material make it difficult to demagnetize with time or heat or other magnetic fields. The invention has a shape that may be easily introduced into the first stomach, but that cannot pass into a cow's lower stomachs, which safely collects metal fragments, while being inexpensive to construct.

Operation—FIGS. 1,2,3

The mineral supplement cow magnet is pushed down the cow's throat. It stays in the first stomach due to its weight and size. It slowly leeches Sr and Fe minerals of the magnet. The Sr is used with Ca to increase bone osteoblasts. Which increase bone growth. The Sr has also been found to stop absorption of the bone by the body know as osteoporosis. The magnet collects metals to keep them from going down into the cow's more delicate second, third and forth stomach. The magnet holds the metal along the magnets length so that sharp edges of metal are covered by round edges of magnet.

Conclusions, Ramifications and Scope

Accordingly the reader will see that the mineral supplement cow magnet invention of this patent is most likely to prevent sickness and death in cows. The need exists, therefore, for a healthy mineral supplement cow magnet. One that is non-toxic, without Aluminum, possessing a relatively strong magnetic field. The polarity pattern is discovered for a SrFe type magnet so that a nail will be held along parallel to the length of the magnet and at the maximum strength. This pole pattern has been discovered to turn a nail parallel to the length of the magnet if the nail is placed on the magnet perpendicular to the length. Furthermore, this pole pattern also prevents a nail from being held along the length of the magnet with the sharp nail tip sticking out the end of the magnet.

The magnetic properties of this material make it difficult to demagnetize with time or heat or other magnetic fields. The invention has a shape that may be easily introduced into the first stomach, but that cannot pass into a cow's lower stomachs, which safely collects metal fragments, while being inexpensive to construct. Furthermore, the cow magnet has the additional advantages in that

- it is one piece;
- it performs the function of cow magnet and mineral supplement;
- it does not use rare metals like Cobalt;
- made of materials that have been tested for ten years in cows and found safe;
- it has overcome prior art magnetization pole pattern problems to reach full effectiveness;
- it is durable to be effective for 30 years in the cows stomach (the average life span of a cow is 15 years);

Although the paragraphs above contain many specifications, these should not be construed as limitating the scope of the invention. For example the pill shape could be achieved in a dog bone shape, ring shape, pretzel shape, or any shape with rounded corners. Thus the scope of the invention should be determined by the claims and their legal equivalents.

I claim:

1. A mineral supplement and cow magnet comprising:

a) Mostly Iron (Fe) and at least one of the non-radioactive, non-toxic, stable Strontium (Sr) forms; containing no (Al) Aluminum or (Pb) Lead;

b) Said magnet in one solid piece, in the shape of an elongated oval pill;

c) Said magnet being of sufficient size and weight to stay in the bovine first stomach; about 0.5" diameter by 3.5" long, about 2.0 to 7.0 ounces;

d) Said magnet being of magnetic strength Bhmax 3.0 MGOe to 40.0 MGOe and Hci of over 2000 Oersteds.

2. The invention of claim 1 having a surface treatment of (Ca) Calcium.

3. The invention of claim 1 having at least 2 opposite magnetic poles oriented through the length and magnetized through the length.

4. The invention of claim 1 having at least 2 opposite poles oriented through the diameter and magnetized across the diameter.

5. The invention of claim 1 having at least 4 magnetic poles oriented across the diameter of said magnet.

* * * * *